United States Statutory Invention Registration [19]

[11] Reg. Number: H49

Levenberg [45] Published: Apr. 1, 1986

[54] PROCESS FOR PRODUCING 3-(2-CHLORO-3,3,3-TRIFLUORO-1-PROPENYL)-2,2-DIMETHYLCYCLOPROPANECARBOXYLATES

[75] Inventor: Patricia A. Levenberg, Langhorne, Pa.

[73] Assignee: FMC Corporation, Philadelphia, Pa.

[21] Appl. No.: 456,663

[22] Filed: Jan. 10, 1983

[51] Int. Cl.[4] ..... C07C 69/74; C07D 301/14; C07D 303/38

[52] U.S. Cl. ..... 560/124; 549/549; 549/525

[58] Field of Search ..... 560/124

[56] References Cited

U.S. PATENT DOCUMENTS

| | | | |
|---|---|---|---|
| 3,998,868 | 12/1976 | Mizutani | 560/124 |
| 4,000,181 | 12/1976 | Elliott | 560/124 |
| 4,024,163 | 5/1977 | Elliott et al. | 560/124 |
| 4,183,948 | 1/1980 | Huff | 560/124 |
| 4,214,004 | 7/1980 | Plummer | 560/124 |
| 4,235,927 | 11/1980 | Engel | 560/124 |
| 4,238,505 | 12/1980 | Engel | 560/124 |
| 4,263,319 | 4/1981 | Engel | 560/124 |
| 4,282,249 | 8/1981 | Roman | 560/124 |
| 4,332,815 | 6/1982 | Engel | 560/124 |
| 4,395,567 | 7/1983 | Engel | 560/124 |
| 4,402,973 | 9/1983 | Plummer | 560/124 |

FOREIGN PATENT DOCUMENTS

| | | | |
|---|---|---|---|
| 0022971 | 1/1981 | European Pat. Off. | 560/124 |
| 2927133 | 1/1981 | Fed. Rep. of Germany . | |

OTHER PUBLICATIONS

Arlt, Angew, Chem. Int. Ed. Engl., 20, pp. 703–713 & 719–722 (1981).

Elliott, Chem. Soc. Rev., 7, pp. 473–475, & 488–493 (1978).

Elliott, Bull. World Health Organ., 44, pp. 315–323 (1971).

Allinger, "Organic Chemistry," p. 458 (1971).

Derwent Abstract No. 02208 D/03 for German Auslegeschrift 3,060,550, patent published Aug. 5, 1982.

Research Disclosure 21903, anonymous, (*Research Disclosure, 219,* Jul. 1982, pp. 239, 240, Industrial Opportunities Ltd., Homewell, Havant, Hampshire. P09 1EF, United Kingdom).

W. G. Taylor, "A Convenient Synthesis of ethyl (±)-cis,trans-3-(2,2-dichlorovinyl)-2,2-Dimethylcyclopropanecarboxylate by the Wittig Reaction", Synthesis, 554 (1980).

W. G. Salmond, "Dichloromethylenetrisdimethylaminophosphorane, Preparation of 1,1-Dichloroolefins from Aldehydes", Tet. Lett. 1239 (1977).

Elliott et al., "The Pyrethrins and Related Compounds, part XVIII, Insecticidal 2,2-Dimethylcyclopropanecarboxylates with New Unsaturated 3-Substituents", J.C.S. Perkin I, 2470 (1974).

Burton et al., "The in situ Generation of $Ph_3P{=}C(CF_3)_2$, A Facile One Pot Conversion of Aldehydes to Bis-trifluoromethyl Olefins", Tet. Lett., 3397 (1979).

Corey et al., "A Synthetic Method for Formyl-Ethynyl Conversion (RCHO→RC≡CH or RC≡CR')", Tet. Lett., 3769 (1972).

Hayashi et al., "Convenient Procedures for Conversion of Carbonyl Compounds to gem-difluoroolefins and their Selective Reductions to Monofluoroolefins", Chem. Lett., 983 (1979).

van Hamm et al., "The Preparation and Reactions of Group IIB Metal Chloride Stabilized Complexes of (Chlorofluoromethylene) tris (Dimethylamino)phosphorane", J. Organomet. Chem., 169, 123 (1979).

*Primary Examiner*—John F. Terapane
*Assistant Examiner*—Howard J. Locker
*Attorney, Agent, or Firm*—Robert M. Kennedy; H. Robinson Ertelt; Robert L. Andersen

[57] ABSTRACT

Disclosed is a Wittig-type process for preparing 3-(2-chloro-3,3,3-trifluoropropenyl)-2,2-dimethylcyclopropanecarboxylates which comprises reacting 1,1,1-trichlorotrifluoroethane with hexamethylphosphorous triamide at a temperature in the range of about −80° C. to 10° C. in the presence of an inert aprotic solvent and a carbonaldehyde ester, and thereafter maintaining the reaction mixture at a temperature in the range of about 0° C. to 30° C. Also disclosed are the novel caronaldehyde ester (2-methyl[1,1'-biphenyl]-3-yl)methyl 2,2-dimethyl-3-formylcyclopropanecarboxylate and a precursor compound, (2-methyl[1,1'-biphenyl]-3-yl)methyl 2,2-dimethyl-3-(1,2-epoxy-2-methylpropyl)cyclopropanecarboxylate, and methods for producing them.

10 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR PRODUCING 3-(2-CHLORO-3,3,3-TRIFLUORO-1-PROPENYL)-2,2-DIMETHYLCYCLOPROPANECARBOXYLATES

This invention pertains to the field of chemical processes; specifically, it pertains to a process for introducing a 2-chloro-3,3,3-trifluoro-1-propenyl group at the C-3 carbon atom of the cyclopropane ring of 2,2-dimethylcyclopropanecarboxylates, and involves a Wittig-type reaction conducted with 1,1,1-trichlorotrifluoroethane, hexamethylphosphorous triamide, and a 2,2-dimethyl-3-formylcyclopropanecarboxylate. It also pertains to novel intermediates and a process for preparing them.

Recently, a number of patents have issued which collectively describe a new and highly important class of pyrethroid insecticides characterized in that the member compounds are 2,2-dimethylcyclopropanecarboxylates having a 2-chloro-3,3,3-trifluoropropenyl substituent at the C-3 carbon atom of the cyclopropane ring. The compounds differ from each other in the identity of the alcohol moiety and are structurally represented by the following formula

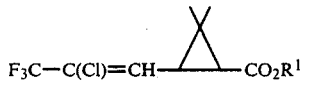

wherein $R^1$ is selected from a diverse group of alcohol radicals including 3-phenoxybenzyl (U.S. Pat. Nos. 4,183,948 and 4,332,815), 5-benzyl-3-furylmethyl (U.S. Pat. Nos. 4,235,927 and 4,332,815), 4-phenyl-2-indanyl (U.S. Pat. No. 4,263,319), and (2-methyl[1,1'-biphenyl]-3-yl)methyl (U.S. Pat. Nos. 4,238,505 and 4,332,815).

The patents above disclose three basic methods for preparing the various chlorotrifluoropropenyl compounds. These methods are illustrated in the equations below wherein R is lower alkyl or $R^1$. Where R is lower alkyl the product is an intermediate, and conversion to the desired insecticidal compound (R is $R^1$) is usually accomplished by conventional procedures, for example, by hydrolysis and reesterification with $R^1$-OH.

METHOD 1—DIAZOACETATE ADDITION TO A DIENE

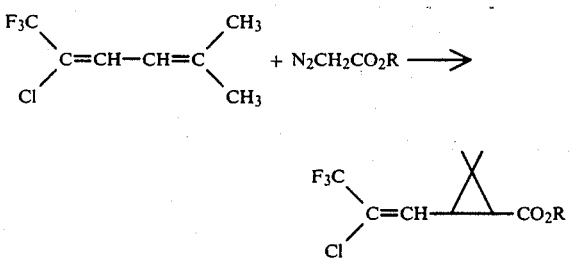

Method 1 is disclosed in U.S. Pat. No. 4,183,948 for preparing the intermediate lower alkyl esters and in U.S. Pat. No. 4,332,815 for either the intermediates or final product insecticides. The method is exemplified for related compounds, but not for the chlorotrifluoropropenyl compounds.

METHOD 2—MALONATE ADDITION TO A DIENE

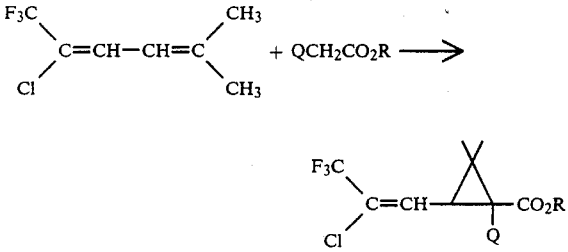

This method is disclosed in U.S. Pat. No. 4,183,948. The group Q is alkoxycarbonyl or cyano, and R is alkyl. The product may be converted into the free acid in which Q is hydrogen by hydrolysis, then into the insecticidal compound by esterification with $R^1$-OH.

METHOD 3—RING CLOSURE OF HALOGENATED HEPTANOATES

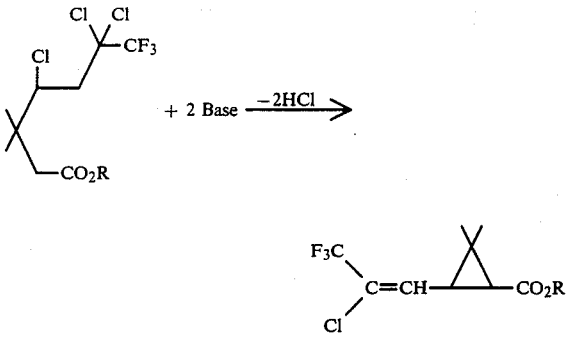

This method involves a base induced sequential or simultaneous di-dehydrochlorination of a 3,3-dimethyl-4,6,6-trichloro-7,7,7-trifluoroheptanoate and is disclosed in all five of the patents cited above.

The present invention provides a further method for preparing 3-(2-chloro-3,3,3-trifluoro-1-propenyl)-2,2-dimethylcyclopropanecarboxylates, including the insecticidal compounds and the intermediate alkyl esters mentioned above.

The process of the invention involves a Wittig-type reaction in which hexamethylphosphorous triamide is employed as the Wittig reagent, and is illustrated in the following chemical equation:

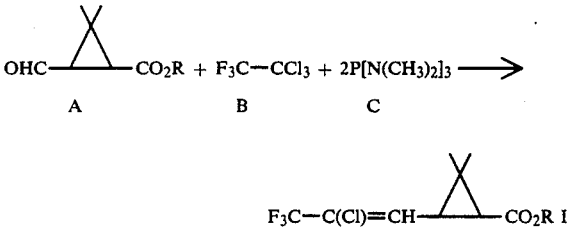

The use of hexamethylphosphorus triamide as a Wittig reagent is well known in the art. Both it and triphenylphosphine have been successfully employed in Wittig-type syntheses of 2,2-dichloroethenylcyclopropanecarboxylates, but neither is believed to have been used, until now, in producing the chlorotrifluoropropenyl compounds of formula I in good yields in a Wittig-type process.

The present process has general utility for the preparation of compounds of formula I. In most applications R will be an alkyl radical of 1 to 6 carbon atoms, usually 1 to 4 carbon atoms especially methyl or ethyl, or a group $R^1$ which represents the radical of an alcohol $R^1$—OH which gives an insecticidal ester when chemically combined with 3-(2-chloro-3,3,3-trifluoro-1-propenyl)-2,2-dimethylcyclopropanecarboxylic acid.

For example, $R^1$ may be allethrolonyl, tetrahydrophthalimidomethyl, 4-phenyl-2-indanyl, or a radical of the formula

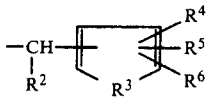

in which $R^2$ is hydrogen, cyano, or ethynyl, $R^3$ is oxygen, sulfur, or vinylene, and $R^4$, $R^5$, and $R^6$ are independently hydrogen, halogen, alkyl or alkenyl of 1 to 4 carbon atoms, phenyl, benzyl, phenoxy, or the group $C_6H_5S(O)_n$—wherein n is 0–2. Most frequently, $R^1$ will be selected from 4-phenyl-2-indanyl, 5-benzyl-3-furylmethyl, 3-phenoxybenzyl, α-cyano-3-phenoxybenzyl, α-cyano-3-phenoxy-4-fluorobenzyl, (2,4-dimethyl[1,1'-biphenyl]-3-yl)methyl, and (2-methyl[1,1'-biphenyl]-3-yl)methyl.

In this application "HMPT" means hexamethylphorphorous triamide, "caronaldehyde" means 2,2-dimethyl-3-formylcyclopropanecarboxylic acid, C/T means cis/trans and refers to the ratio of cis isomers to trans isomers present in the indicated compound by virtue of geometric isomerism about the cyclopropane ring, and E/Z refers to the ratio of E isomers to Z isomers present by virtue of geometric isomerism about the double bond of the chlorotrifluoropropenyl group in compounds of formula I.

The present process comprises reacting 1,1,1-trichlorotrifluoroethane with HMPT at a temperature in the range of about −80° C. to 10° C. in the presence of an inert aprotic solvent and a caronaldehyde ester of the formula

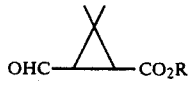

where R is defined as above, and thereafter maintaining the reaction mixture at a temperature in the range of about 0° C. to 30° C. to give the chlorotrifluoropropenyl compound of formula I.

While no attempt was made to determine the mechanism of the chemical reaction involved in the present process, the results obtained are consistent with a normal Wittig pathway in which 1,1,1-trichlorotrifluoroethane and HMPT react to form an ylid which, concomitant with its formation, reacts with the caronaldehyde ester to form an adduct which decomposes on standing to produce the compound of formula I.

Formation of the ylid and its reaction with the caronaldehyde ester are believed to occur very rapidly during the initial temperature phase of the process. Data are presented in Table 1 below for initial phase reaction times in the range of 15 minutes to 3 hours at temperatures in the range of −78° C. to 0° C. The ylid is believed to be a thermally unstable species, and a low initial temperature is indicated to slow the rate of decomposition sufficiently so that the desired reaction between the ylid and the caronaldehyde ester can occur prior to substantial ylid decomposition. Having the caronaldehyde ester present at the outset, during ylid formation, is felt to reduce the opportunity for ylid decomposition by allowing the desired reaction to occur directly upon ylid formation. In fact, substantially reduced yields of desired product may result if the caronaldehyde ester is added last to the reaction vessel, even where such addition is made promptly following the addition of the HMPT and trichlorotrifluoroethane. In a preferred embodiment, the HMPT is added to a mixture of the trichlorotrifluoroethane and caronaldehyde ester.

The adduct produced from the ylid and the caronaldehyde ester is also thermally unstable, and decomposes on standing to give the desired product, the compound of formula I. This conversion, which constitutes the terminal phase of the process, is believed to occur primarily at the higher temperature range, about 0° C. to 30° C.

While it is possible under the stated conditions to conduct the process at a uniform temperature throughout, or at a higher temperature during the initial phase than that used in the terminal phase, such embodiments are not preferred and may give reduced yields of desired product. Because of ylid instability, it is advantageous to select a temperature in the range of about −80° C. to 0° C., preferably up to only about −30° C. or even −50° C., for the initial phase of the process during which the ylid-aldehyde adduct species is formed. Once the adduct is formed it is advantageous to raise the temperature, preferably to about 15° C. to 30° C., to facilitate conversion to the desired product and to drive the reaction to completion.

The stoichiometry of the process theoretically requires one mole of 1,1,1-trichlorotrifluoroethane and two moles of HMPT for each mole of caronaldehyde ester used. The second molar equivalent of HMPT is employed to scavenge the two chlorine ions eliminated from each molecule of the trichlorotrifluoroethane in forming the ylid. In practice, it is desirable to use an excess of the trichlorotrifluoroethane, HMPT, or both; preferably from about 1.1 to 2 moles of the trichlorotrifluoroethane and from about 2.2 to 3 moles of HMPT for each mole of caronaldehyde ester used. Very satisfactory results have been obtained where the three reactants were employed in the molar ratio 1/1.1/2.5.

The prior art discloses the use of zinc dust as an adjuvant in Wittig-type reactions. It has been used with either triphenylphosphine or HMPT Wittig reagent, generally in a molar equivalent amount or a slight excess with respect to the aldehyde. By complexing with the Wittig reagent, the zinc dust additive presumably aids in ylid formation, reduces the amount of Wittig reagent required, and generally gives increased yields. In some instances, the presence of zinc dust is critical for the reaction to proceed at all. An important aspect of the present process is that the presence of zinc dust is not required either for operation of the process per se or for satisfactory yields to be realized. The yields of desired product are generally comparable for the present process conducted with and without zinc dust. Compare runs 23–25 (zinc dust added) with runs 12–15 in Table 1 below.

The process is conducted in the presence of an inert aprotic solvent, preferably under an inert atmosphere. The various aprotic solvents normally used in Wittig reactions are generally suitable for use here. Usually, the solvent will be selected from among aliphatic hydrocarbons of 5 to 8 carbon atoms; aromatic hydrocarbons of 6 ring carbon atoms, optionally substituted with from 1 to 3 substituents selected from alkyl of 1 or 2 carbon atoms and chlorine, for example toluene, xylene, or chlorobenzene; ethers selected from diethyl ether, 1,2-dimethoxyethane, bis-(2-methoxyethyl)ether, tetrahydrofuran, and dioxane, particularly diethyl ether or tetrahydrofuran; methylene chloride; methyl or ethyl acetate; acetonitrile; dimethylformamide; dimethylacetamide; hexamethylphosphoric triamide; N-methylpyrrolidinone; and mixtures of any of the above. The E/Z ratio in the chlorotrifluoropropenyl product appears to depend somewhat upon the polarity of the solvent used. Data are presented in Table 1 below which show that the E/Z ratio in the product decreases as solvent polarity increases in the series methylene chloride, toluene, dimethylformamide/methylene chloride mixture, dimethyl sulfoxide, acetonitrile.

The 1,1,1-trichlorotrifluoroethane and HMPT starting materials for the present process are readily available in commerce. The caronaldehyde esters may be prepared by ozonolysis of the isobutenyl side chain of an appropriate chrysanthemic acid ester in accordance with the method described by Elliott et al., in U.S. Pat. No. 4,024,163. The caronaldehyde esters may also be prepared by epoxidation of the isobutenyl group of an appropriate chrysanthemate, and oxidation of the resulting epoxide compound as illustrated in the schema below for 2-methyl[1,1'-biphenyl]-3-ylmethyl caronaldehyde.

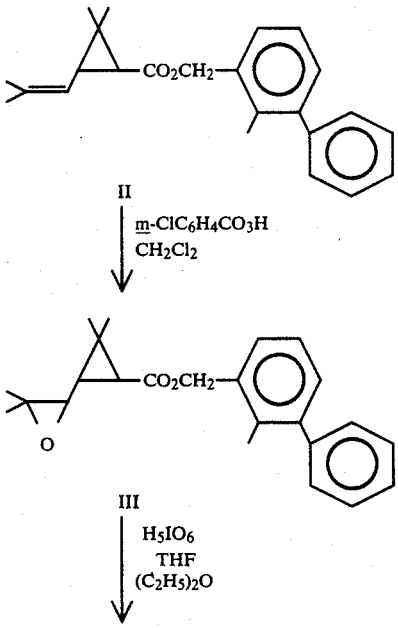

-continued

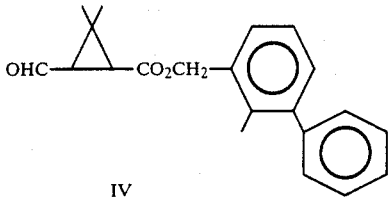

IV

The 2-methyl[1,1'-biphenyl]methyl chrysanthemate, compound II, is treated with an epoxidizing agent such as m-chloroperbenzoic acid in methylene chloride or other inert solvent to give the corresponding epoxide compound III. Conversion of the epoxide compound to the caronaldehyde ester IV is accomplished by periodic acid oxidation in the presence of a mixture of diethyl ether and tetrahydrofuran. The 2-methyl[1,1'-biphenyl]methyl chrysanthemate, II, can be prepared by hydrolysis of the corresponding ethyl ester and reaction of the resulting free acid with 3-chloromethyl-2-methyl[1,1'-biphenyl] in the presence of a strong base such as 1,8-diazabicyclo[5.4.0]undec-7-ene (DBU). Ethyl caronaldehyde may be converted in similar fashion to 2-methyl[1,1'-biphenyl]methyl caronaldehyde, IV. Compounds III and IV are novel intermediates and comprise a further aspect of the present invention.

The Examples which follow illustrate the process of the present invention in accordance with the general method described above. In the Examples, temperatures are in degrees Celsius, pressures are in mm Hg, and reduced pressure for concentrations of liquid was produced by a vacuum pump unless otherwise specified.

EXAMPLE I

Synthesis of Ethyl cis,trans-3-(2-chloro-3,3,3-trifluoro-1-propenyl)-2,2-dimethylcyclopropanecarboxylate Under a dry nitrogen atmosphere, a stirred solution of 6.8 g (40 mmoles) of ethyl 2,2-dimethyl-3-formylcyclopropanecarboxylate (C/T 20/80) and 6.0 ml (45 mmoles) of 1,1,1-trichlorotrifluoroethane in 100 ml of dry tetrahydrofuran was cooled to −78° C. in a dry ice/acetone bath. A solution of 18.2 ml (98.0 mmoles) of hexamethylphosphorous triamide in 20 ml of tetrahydrofuran was added dropwise to the reaction mixture over 15 minutes. After complete addition the mixture was stirred at −78° C. for one hour, then was allowed to warm to room temperature and was stirred for 18 hours. The mixture was diluted with 300 ml of diethyl ether and washed in succession with 75 ml of a saturated aqueous solution of ammonium chloride, 100 ml of 1N hydrochloric acid, and 50 ml of a saturated aqueous solution of sodium chloride. The organic phase was dried over anhydrous magnesium sulfate, filtered, and the solvent removed by evaporation under reduced pressure to leave an oil. Purification of the oil by distillation under reduced pressure produced 8.76 g of ethyl cis,trans- 3-(2-chloro-3,3,3-trifluoro-1-propenyl)-2,2-dimethylcyclopropanecarboxylate, b.p. 68°–83° C. at 0.55 mm Hg, 81.0% yield, 96.7% pure by glc, 78.3% effective yield (96.7% of 81.0%), C/T 14:86 and E/Z 41:59 as determined by nmr analysis.

This reaction was repeated a number of times. The reaction conditions for each run are given below in Table 1*a*, and the results in Table 1*b*. The particular run described in Example I is reported as run 9 in the tables below. The general procedure used in Example I was used throughout except where otherwise indicated. Notable deviations from the Example I procedure were made in runs 21 and 22 where different order of addition was employed, and runs 23–25 which were conducted in the presence of zinc dust.

TABLE 1a

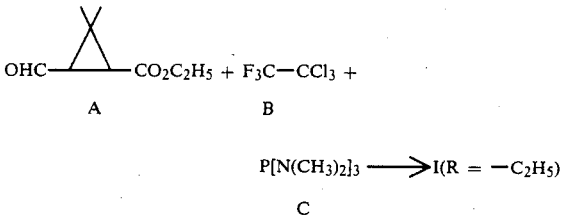

| Run # | Reactants[1] Molar Ratio[2,3] | Reaction Conditions: Solvent | Temp.[4] (°C.)/ Time (Hr.) |
|---|---|---|---|
| 1 | 1/1.9/2.5 | $CH_2Cl_2$ | −30/1; RT/5 |
| 2 | 1/1.1/2.5 | $CH_2Cl_2$ | −25/1.5; RT/22 |
| 3 | 1/2.1/2.5 | DMF/$CH_2Cl_2$(5/1) | −30/2; RT/20 |
| 4 | 1/1.1/2.5 | $C_6H_5CH_3$ | −30/0.5; RT/18 |
| 5 | 1/1.1/2.5 | $C_6H_5CH_3$ | −25/0.25; RT/4.5 |
| 6 | 1/1.1/2.5 | n-$C_5H_{12}$ | −20/2; RT/22 |
| 7 | 1/1.1/2.5 | $(C_2H_5)_2O$ | −25/1; RT/20 |
| 8 | 1/1.1/2.5 | THF | −78/1.25; RT/18 |
| 9 | 1/1.1/2.5 | THF | −78/1; RT/18 |
| 10 | 1/1.1/2.5 | THF | −70/1; RT/18 |
| 11 | 1/1.1/2.5 | THF | −50/3; RT/17 |
| 12 | 1/1.1/2.5 | THF | −30/7; RT/18 |
| 13 | 1/1.1/2.5 | THF | −30/1; RT/66 |
| 14 | 1/1.1/2.5 | THF | −30/1; RT/36 |
| 15 | 1/1.1/2.5 | THF | −30/1; RT/18 |
| 16 | 1/1.1/2.5 | THF | 0/2; RT/18 |
| 17 | 1/1.1/2.5 | $CH_3CO_2C_2H_5$ | −25/1; RT/20 |
| 18 | 1/2.3/2.5 | $(CH_3)_2SO$ | −20/0.25; RT/6.5 |
| 19 | 1/1.1/2.5 | $CH_3CN$ | −30/1; RT/18 |
| 20 | 1/2.1/2.5 | $CH_3CN$ | −30/0.5; RT/5 |
| 21[5] | 1/1.1/2.5 | THF | −30/2; RT/18 |
| 22[6] | 1/1.1/2.5 | THF | −30/2; RT/18 |
| 23[7] | 1/1.1/2.5 | THF | −30/2; RT/18 |
| 24[7] | 1/1.1/2.5 | THF | −30/2; RT/18 |
| 25[7] | 1/1.1/2.5 | THF | −30/1; RT/18 |

[1]C/T ratio of reactant A was not determined for run 4 and was 20:80 for runs 8, 9, and 13 and 30:70 for all other runs.
[2]A/B/C
[3]Twenty mmoles of A was used in run 13, 24.6 mmoles in run 4, and 40 mmoles in all other runs.
[4]RT is room temperature.
[5]Order of addition: A was added to a mixture of B and C.
[6]Order of addition: B was added to a mixture of A and C.
[7]The reaction was conducted in the presence of zinc dust, a 5% molar excess of zinc being used based on the amount of reactant A used.

TABLE 1b

| Run # | Product Data: % Distilled Yield[1] | % Purity[2] | % Effective Yield[3] | C/T[4] | E/Z[4] |
|---|---|---|---|---|---|
| 1 | 56.4 | 75.9 | 42.8 | 30:70 | 37:63 |
| 2 | 53.6 | 97.9 | 52.5 | 20:80 | 34:66 |
| 3 | 41.6 | 89.8 | 37.4 | 21:79 | 17:83 |
| 4 | 37.8 | 96.4 | 36.4 | — | 34:66 |
| 5 | 55.4 | 97.6 | 54.1 | 36:64 | 33:67 |
| 6 | 30.5 | 94.5 | 28.9 | 49:51 | 31:69 |
| 7 | 48.4 | 98.0 | 47.4 | 34:66 | 25:75 |
| 8 | 75.0 | 98.9 | 74.2 | 16:84 | 41:59 |
| 9 | 81.0 | 96.7 | 78.3 | 14:86 | 41:59 |
| 10 | 57.8 | 97.3 | 56.2 | 28:72 | 29:71 |
| 11 | 59.9 | 92.7 | 55.5 | 24:76 | 34:66 |
| 12 | 51.5 | 93.8 | 48.3 | 31:69 | 33:67 |
| 13 | 65.1 | 97.8 | 63.7 | 15:85 | 34:66 |
| 14 | 58.2 | 98.0 | 57.0 | 22:78 | 38:62 |
| 15 | 60.5 | 99.6 | 60.3 | 17:83 | 38:62 |
| 16 | 46.9 | 98:3 | 46.1 | 34:66 | 34:66 |
| 17 | 49.3 | 98.2 | 48.4 | 21:79 | 35:65 |
| 18 | 24.0 | 74.0 | 17.8 | 24:76 | 15:85 |

TABLE 1b-continued

| Run # | Product Data: % Distilled Yield[1] | % Purity[2] | % Effective Yield[3] | C/T[4] | E/Z[4] |
|---|---|---|---|---|---|
| 19 | 50.8 | — | — | 20:80 | 9:91 |
| 20 | 51.8 | 86.8 | 45.0 | 21:79 | 8:92 |
| 21 | 86.3[5] | 23.2[5] | 20.0[5] | — | — |
| 22 | 31.5 | 97.1 | 30.6 | 40:60 | 35:65 |
| 23 | 56.6 | 96.1 | 54.4 | 30:70 | 32:68 |
| 24 | 62.9 | 94.9 | 59.7 | 30:70 | 32:68 |
| 25 | 47.2 | 93.4 | 44.1 | 12:88 | 42:58 |

[1]Based on weight of distillate obtained and is not corrected for purity.
[2]The percent content of ethyl 3-(2-chloro-3,3,3-trifluoro-1-propenyl)-2,2-dimethylcyclopropanecarboxylate in the distillate as determined by glc analysis.
[3]The percent distilled yield corrected for purity.
[4]Calculated from nmr data.
[5]Product was not distilled; figures are based on undistilled product.

EXAMPLE II

Synthesis of (2-methyl[1,1'-biphenyl]-3-Yl)methyl cis,trans-3-(2-chloro-3,3,3,-trifluoro-1-propenyl)-2,2-dimethylcyclopropane carboxylate

A. Preparation of cis,trans-2,2-dimethyl-3-(2-methyl-1-propenyl)cyclopropanecarboxylic acid as an intermediate To a stirred solution of 20.0 g (102 mmoles) of ethyl cis,trans-2,2-dimethyl-3-(2-methyl-1-propenyl)cyclopropanecarboxylate (C/T=40/60) in 200 ml of ethanol was added a solution of 4.69 g (117 mmoles) of sodium hydroxide in 55 ml of water. After complete addition, the mixture was heated at reflux for 6.5 hours, then cooled, diluted with water, and washed with 100 ml of diethyl ether. The aqueous phase was acidified to a pH of 1 with 6M hydrochloric acid, then extracted with four 150 ml portions of diethyl ether. The extracts were combined, washed with two 50 ml portions of a saturated aqueous sodium chloride solution, dried over anhydrous magnesium sulfate, and filtered. The filtrate was evaporated under reduced pressure to yield 12.88 g of cis,trans-2,2-dimethyl-3-(2-methyl-1-propenyl)cyclopropanecarboxylic acid (C/T=40/60) as an oil which solidified on standing.

B. Preparation of (2-methyl[1,1'-biphenyl]-3-yl)methyl cis,trans-3-(2-methyl-1-propenyl)-2,2-dimethylcyclopropanecarboxylate as an intermediate Under a dry nitrogen atmosphere a solution of 18.3 g (84.4 mmoles) of 3-chloromethyl-2-methyl[1,1'-biphenyl]in 60 ml of dry acetonitrile was added dropwise to a stirred mixture of 12.88 g (76.7 mmoles) of cis,trans-2,2-dimethyl-3-(2-methyl-1-propenyl)- cyclopropanecarboxylic acid (C/T=40/60) and 12.6 ml (84.4 mmoles) of 1,8-diazabicyclo[5.4.0]undec-7-ene in 75 ml of dry acetronitrile. After complete addition, the mixture was stirred at room temperature for 21 hours, then diluted with 300 ml of diethyl ether and washed in succession with two 30 ml portions of 1N aqueous hydrochloric acid and one 50 ml portion of a saturated aqueous sodium chloride solution. The organic phase was dried over anhydrous magnesium sulfate and filtered. The filtrate was evaporated under reduced pressure to yield 25.07 g of (2-methyl- [1,1'-biphenyl]-3-yl)methyl cis,trans-3-(2-methyl-1-propenyl)-2,2-dimethylcyclopropanecarboxylate (C/T=40/60) as an oil.

C. Preparation of (2-methyl[1,1'-biphenyl]-3-yl)methyl cis,trans-2,2-dimethyl-3-(1,2-epoxy-2-methylpropyl) cyclopropanecarboxylate as an intermediate A stirred solution of 25.07 g (72.04 mmoles) of (2-methyl-[1,1'-biphenyl]-3-yl)methyl cis,trans-3-(2-methyl-1-propenyl)-2,2-dimethylcyclopropanecarboxylate (C/T=40/60) in 175 ml of methylene chloride was cooled to 0° C. Sodium bicarbonate (9.55 g, 101.7 mmoles) was added to the reaction mixture followed by 17.55 g (101.7 mmoles) of 85% m-chloroperbenzoic acid which was added portionwise. After complete addition, the reaction mixture was stirred at 0° C. for 0.5 hour, then heated at reflux for 17.5 hours. The mixture was cooled to room temperature and filtered. The filtrate was diluted to about 450 ml with methylene chloride and washed in succession with two 50 ml portions of aqueous 1N sodium hydroxide, 100 ml of an aqueous 10% sodium sulfite solution, and 80 ml of a saturated aqueous sodium chloride solution. The organic phase was dried over anhydrous magnesium sulfate and filtered. The filtrate was evaporated under reduced pressure to yield 26.4 g of (2-methyl[1,1'-biphenyl]-3-yl)methyl cis,trans-2,2-dimethyl-3-(1,2-epoxy-2-methylpropyl)cyclopropanecarboxylate (C/T=40/60) as an oil.

NMR ($CDCl_3$) ppm (δ): 1.17–1.33 (m,12H); 1.5–2.8 (m,3H);
2.20 (s,3H); 5.13–5.30 (m,2H); 7.15–7.43 (m,8H).

D. Preparation of (2-methyl[1,1'-biphenyl]-3-yl)methyl cis,trans-2,2-dimethyl-3-formylcyclopropanecarboxylate as an intermediate A stirred solution of 26.4 g (72.4 mmoles) of (2-methyl[1,1'-biphenyl]-3-yl)methyl cis,trans-2,2-dimethyl-3-(1,2-epoxy-2-methylpropyl)cyclopropanecarboxylate (C/T=40/60) in 75 ml of diethyl ether was cooled to 0° C. A solution of 16.5 g (72.4 mmoles) of periodic acid in 85 ml of diethyl ether and 41 ml of tetrahydrofuran was added dropwise to the reaction mixture during 35 minutes. After complete addition, the mixture was stirred at 0° C. for one hour. A saturated aqueous solution of sodium bicarbonate was added to the reaction mixture until a pH of 7 was obtained. The mixture was extracted with two 200 ml portions of diethyl ether. The organic phase was washed with 100 ml of a saturated aqueous sodium chloride solution, dried over anhydrous magnesium sulfate and filtered. The filtrate was evaporated under reduced pressure to yield 24.02 g of (2-methyl[1,1'-biphenyl]-3-yl)methyl cis,trans-2,2-dimethyl-3-formylcyclopropane-carboxylate as an oil, C/T 43/57 as determined by nmr analysis.

NMR ($CDCl_3$) ppm (δ):1.2–1.4 (m,6H); 1.60 (s,0.87H,cis); 2.20
(s,3H); 2.55 (d,1.13H,trans); 5.23 (s,2H);
7.15–7.43 (m,8H); [9.42 (t,J=2 Hz,trans)
and 9.63 (d,J=6 Hz,cis), 1H].

E. Preparation of (2-methyl[1,1'-biphenyl]-3-yl)methyl cis,trans-3-(2-chloro-3,3,3-trifluoro-1-propenyl)-2,2-dimethylcyclo-propanecarboxylate Under a dry nitrogen atmosphere a stirred solution of 0.5 g (1.55 mmoles) of (2-methyl[1,1'-biphenyl]-3-yl)methyl cis,trans-2,2-dimethyl-3-formylcyclopropanecarboxylate (C/T 43/57) and 0.3 ml (2.25 mmoles) of 1,1,1-trichlorotrifluoroethane in 6 ml of dry tetrahydrofuran was cooled to −35° C. A solution of 0.71 ml (3.8 mmoles) of hexamethylphosphorous triamide in 2.0 ml of tetrahydrofuran was added dropwise to the reaction mixture. After complete addition, the mixture was stirred at −30° C. for 1.25 hour, then was allowed to warm to room temperature and was stirred for 19 hours. The mixture was diluted with 150 ml of diethyl ether and washed in succession with 20 ml of a saturated aqueous solution of ammonium chloride, 40 ml of 1N hydrochloric acid, and 20 ml of a saturated aqueous solution of sodium chloride. The organic phase was dried over anhydrous magnesium sulfate, filtered, and the solvent evaporated under reduced pressure to leave an orange oil, 0.55 g, 84.0% yield, 89% pure by glc. The oil was subjected to column chromatography on silica gel, eluting with n-pentane/diethyl ether (3:1). The appropriate fractions were combined and the solvent evaporated to yield 0.25g (38.2% yield) of (2-methyl[1,1'-biphenyl]-3-yl)methyl cis,trans-3-(2-chloro-3,3,3-trifluoro-1-propeny)-2,2-dimethylcyclo-propanecarboxylate as an oil, C/T 39:61 by nmr, E/Z 42:58 by nmr.

In a second run, the reaction of 0.5 g (1.55 mmoles) of the caronaldehyde ester (C/T 43/57), 0.3 ml (2.25 mmoles) of 1,1,1-trichlorotrifluoroethane, and 0.71 ml (3.8 mmoles) of HMPT, conducted in the presence of 10 ml of tetrahydrofuran at a temperature of −30° C. for 2 hours then at room temperature for 18 hours, gave, after adsorption chromatography on silica gel eluting with 3:1 pentane:diethyl ether, 0.26 g (39.7% yield) of the expected product, C/T 47:53 by nmr, E/Z 44:56 by nmr.

In a further run, the reaction of 0.59 g (1.8 mmoles) of the caronaldehyde ester (C/T 5/95), 0.3 ml (2.25 mmoles) of 1,1,1-trichlorotrifluoroethane, and 0.82 ml (4.4 mmoles) of HMPT, conducted in the presence of 7.5 ml of tetrahydrofuran at a temperature of −25° C. for 1 hour then at room temperature for 18 hours, gave, after adsorption chromatography on silica gel eluting with 3:1 pentane-diethyl ether, 0.17 g (22.4% yield) of the desired product, C/T 5:95 by nmr, E/Z 30:70 by nmr.

I claim:

1. The compound of the formula

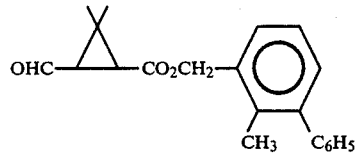

2. The compound of the formula

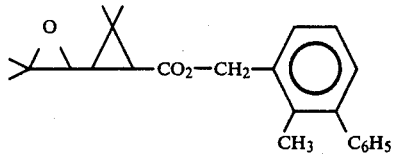

3. A process for preparing a chlorotrifluoropropenyl compound of the formula

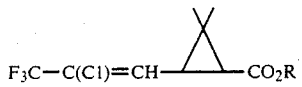

wherein R is an alkyl radical of 1 to 6 carbon atoms or the group $R^1$ which is allethrolonyl, tetrahydrophthalimidomethyl, 4-phenyl-2-indanyl, or is represented by the formula

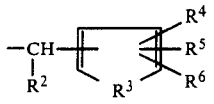

in which $R^2$ is hydrogen, cyano, or ethynyl, $R^3$ is oxygen, sulfur, or vinylene, and $R^4$, $R^5$, and $R^6$ are independently hydrogen, halogen, alkyl or alkenyl of 1 to 4 carbon atoms, phenyl, benzyl, phenoxy, or the group $C_6H_5S(O)n$- wherein n is 0–2, which comprises reacting 1,1,1-trichlorotrifluoroethane with hexamethylphosphorous triamide at a temperature in the range of about −80° C. to 10° C. in the presence of an inert aprotic solvent and a caronaldehyde ester of the formula

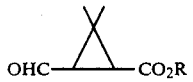

wherein R is defined as above, and thereafter maintaining the reaction mixture at a temperature in the range of about 0° C. to 30° C. to yield the chlorotrifluoropropenyl compound, at least one molar portion of 1,1,1-trichlorotrifluoroethane and two molar portions of hexamethylphosphorous triamide being used for each molar portion of caronaldehyde ester used.

4. The process of claim 3 wherein the aprotic solvent is selected from the group consisting of aliphatic hydrocarbons of 5 to 8 carbon atoms; aromatic hydrocarbons having 6 ring carbon atoms, optionally substituted with from 1 to 3 substituents selected from alkyl of 1 or 2 carbon atoms and chlorine; ethers selected from diethyl ether, 1,2-dimethoxyethane, bis-(2-methoxyethyl) ether, tetrahydrofuran, and dioxane; methylene chloride; methyl or ethyl acetate; acetonitrile; dimethylformamide; dimethylacetamide; hexamethylphosphoric triamide; N-methylpyrrolidinone; and mixtures of any of the above.

5. The process of claim 4 wherein the reaction of 1,1,1- trichlorotrifluoroethane with hexamethylphosphorous triamide is conducted at a temperature in the range of about −80° C. to 0° C., and the temperature is then raised to a figure in the range of about 15° C. to 30° C. to give the chlorotrifluoropropenyl compound.

6. The process of claim 5 wherein the initial temperature range is −80° C. to −30° C.

7. The process of claim 6 wherein from about 1.1 to 2 molar portions of trichlorotrifluoroethane and about 2.2 to 3 molar portions of hexamethylphosphorous triamide are used for each molar portion of caronaldehyde ester used.

8. The process of claim 7 wherein R is an alkyl radical of 1 to 4 carbon atoms or the group $R^1$ which is (2-methyl[1,1′-biphenyl]-3-yl)methyl.

9. A process for preparing a chlorotrifluoropropenyl compound of the formula

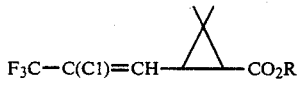

wherein R is an alkyl radical of 1 to 4 carbon atoms or the group $R^1$ which is (2-methyl[1,1′-biphenyl]-3-yl)methyl, which comprises reacting 1,1,1-trichlorotrifluoroethane with hexamethylphosphorous triamide in the presence of a caronaldehyde ester of the formula

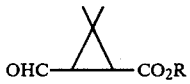

wherein R is as defined above, and an inert aprotic solvent selected from the group consisting of aliphatic hydrocarbons of 5 to 8 carbon atoms, toluene, xylene, diethyl ether, tetrahydrofuran, methylene chloride, ethyl acetate, acetonitrile, and dimethylformamide, at a temperature in the range of about −80° C. to 0° C., and thereafter raising the temperature to a figure in the range of about 15° C. to 30° C. to form the chlorotrifluoropropenyl compound, about 1.1 to 2 molar portions of 1,1,1-trichlorotrifluoroethane and about 2.2 to 3 molar portions of hexamethylphosphorous triamide being used for each molar portion of caronaldehyde ester used.

10. The process of claim 9 wherein R is the group $R^1$.

* * * * *